United States Patent
Katscher et al.

(10) Patent No.: US 12,019,134 B2
(45) Date of Patent: Jun. 25, 2024

(54) MR ELECTRIC PROPERTIES TOMOGRAPHY WITHOUT CONTRAST AGENT

(71) Applicant: KONINKLIJKE PHILIPS N.V., Eindhoven (NL)

(72) Inventors: Ulrich Katscher, Norderstedt (DE); Johan Samuel Van Den Brink, Meteren (NL); Jochen Keupp, Rosengarten (DE)

(73) Assignee: Koninklijke Philips N.V., Eindhoven (NL)

( * ) Notice: Subject to any disclaimer, the term of this patent is extended or adjusted under 35 U.S.C. 154(b) by 188 days.

(21) Appl. No.: 17/617,955

(22) PCT Filed: Jun. 19, 2020

(86) PCT No.: PCT/EP2020/067092
§ 371 (c)(1),
(2) Date: Dec. 10, 2021

(87) PCT Pub. No.: WO2020/254571
PCT Pub. Date: Dec. 24, 2020

(65) Prior Publication Data
US 2022/0308148 A1   Sep. 29, 2022

(30) Foreign Application Priority Data

Jun. 20, 2019   (EP) .................... 19181445

(51) Int. Cl.
*G01R 33/561*   (2006.01)
*A61B 5/00*   (2006.01)
(Continued)

(52) U.S. Cl.
CPC .......... *G01R 33/5613* (2013.01); *A61B 5/004* (2013.01); *A61B 5/0536* (2013.01);
(Continued)

(58) Field of Classification Search
None
See application file for complete search history.

(56) References Cited

U.S. PATENT DOCUMENTS

| | | | |
|---|---|---|---|
| 2014/0184219 A1* | 7/2014 | Kim ...................... | G01R 33/48 324/309 |
| 2015/0051475 A1* | 2/2015 | Leussler ............ | A61B 18/1815 600/411 |
| 2018/0011158 A1* | 1/2018 | Katscher .............. | G01R 33/443 |

FOREIGN PATENT DOCUMENTS

EP   3378426 A1   9/2018

OTHER PUBLICATIONS

Heid et al "Multi Echo True FISP Imaging" Proceedings of the 3rd Annual Meeting of ISMRM, Aug. 19, 1994.
(Continued)

*Primary Examiner* — Rodney E Fuller

(57) ABSTRACT

A method of magnet resonance (MR) imaging of an object includes MR signal acquisition in a single scan providing information for electric properties imaging (EPT), which may include a phase map as well as tissue boundaries. The method includes: subjecting the object to a multi echo steady state imaging sequence or a fast spectroscopic imaging sequence that includes RF pulses and switched magnetic field gradients, wherein two or more echo signals are generated after each RF excitation; acquiring the echo signals; deriving a magnitude image and a phase map from the acquired echo signals, which phase map represents the spatial RF field distribution induced by the RF pulses in the object; and reconstructing an electric conductivity map from the magnitude image and from the phase map, wherein tissue boundaries are derived from at least the magnitude image.

9 Claims, 2 Drawing Sheets

(51) Int. Cl.
  *A61B 5/0536* (2021.01)
  *G01R 33/56* (2006.01)
  *G01R 33/563* (2006.01)

(52) U.S. Cl.
  CPC ..... *G01R 33/5607* (2013.01); *G01R 33/5608* (2013.01); *G01R 33/5615* (2013.01); *G01R 33/56341* (2013.01)

(56) References Cited

OTHER PUBLICATIONS

Nehrke et al "Dream—A Novel Approach for Robust Ultrafast MultiSlice B1 Mapping" Magnetic Reson in Med. vol. 68 No. 5, Nov. 1, 2012 p. 1517-1526.
Katscher et al "Electric Properties Tomography Biochemical Physical and Technical Background Evaluation and Clinical Applications" NMR in Med, vol. 30, No. May 8, 24, 2017.
Medved et al "High Resolution Spatial and Spectral Imaging Aids" Proc. of the Int. Soc. for Magnetic Reson. in Med. May 4, 2002.
Lee et al "Current Induced Alternating Reversed Dual-Steady State for Joint Estimationof Tissue Relaxation and Electrical Properties" Magnetic Reson. in Med. vol. 78 No. 1 Aug. 4, 2016.
Enz et al "Simultaneous B1 and B0 Mapping Using Dual Echo Actual Flip Angle Imaging" Proceedings of the Int. Soc. for Magnetic Reson, in Med. Apr. 23, 2011.
Granlund et al "High Resolution Three Dimensional Diffusion Weighted Breast Imaging Using DESS" Magnetic Reson Imaging, 2014 p. 330-341.
Kraff et al. "7 Tesla Quantitative HIP MRI: a Comparison Between TESS and CPMG for T2 Mapping" Magnetic Resonance Materials in Physics, 2016 p. 503-512.
International Search Report and Written Opinion From PCT/EP2020/067092 dated Dec. 24, 2020.
Mori N et al., Diagnostic value of electric properties tomography (EPT) for differentiating benign from malignant breast lesions: comparison with standard dynamic contrast-enhanced MRI. Eur Radiol. Sep. 25, 2018. doi: 10.1007/s00330-018-5708-4.
Gras V, Farrher E, Grinberg F, Shah NJ. Diffusion-weighted DESS protocol optimization for simultaneous mapping of the mean diffusivity, proton density and relaxation times at 3 Tesla. Magn Reson Med. 2017;78:130-141.
Medved M et al., Non-contrast enhanced MRI for evaluation of breast lesions: comparison of non-contrast enhanced high spectral and spatial resolution (HiSS) images vs. contrast enhanced fat-suppressed images. Acad Radiol. 2011; 18: 1467-1474.
Yamada T et al. Comparison of detectability of breast cancer by abbreviated breast MRI based on diffusion-weighted images and postcontrast MRI. Jpn J Radiol. May 2018; 36(5):331-339.
Scheffler K, Hennig J. Is TrueFISP a gradient-echo or a spin-echo sequence? Magn Reson Med. Feb. 2003;49(2):395-7.
Zur Y, Stokar S, Bendel P. An analysis of fast imaging sequences with steady-state transverse magnetization refocusing. Magn. Reson. Med. 1988;6:175-193.

* cited by examiner

MR ELECTRIC PROPERTIES TOMOGRAPHY WITHOUT CONTRAST AGENT

CROSS REFERENCE TO RELATED APPLICATIONS

This application is a U.S. national phase application of International Application No. PCT/EP2020/067092 filed on Jun. 19, 2020, which claims the benefit of EP Application Serial No. 19181445.8 filed on Jun. 20, 2019 and is incorporated herein by reference.

FIELD OF THE INVENTION

The invention relates to the field of magnetic resonance (MR) imaging. It concerns a method of MR imaging of an object. The invention also relates to a MR device and to a computer program to be run on a MR device.

BACKGROUND OF THE INVENTION

Image-forming MR methods which utilize the interaction between magnetic fields and nuclear spins in order to form two-dimensional or three-dimensional images are widely used nowadays, notably in the field of medical diagnostics, because for imaging of soft tissue they are superior to other imaging methods in many respects, do not require ionizing radiation and are usually not invasive.

According to the MR method in general, the object, for example the body of the patient to be examined, is arranged in a strong, uniform magnetic field (commonly referred to as $B_0$) whose direction at the same time defines an axis (normally the z-axis) of the co-ordinate system on which the measurement is based. The magnetic field produces different energy levels for the individual nuclear spins in dependence on the magnetic field strength which can be excited (spin resonance) by application of an electromagnetic alternating field (RF field, commonly referred to as $B_1$) of defined frequency (so-called Larmor frequency, or MR frequency). From a macroscopic point of view, the distribution of the individual nuclear spins produces an overall magnetization which can be deflected out of the state of equilibrium by application of an electromagnetic pulse of appropriate frequency (RF pulse), so that the magnetization performs a precessional motion about the z-axis. The precessional motion describes a surface of a cone whose angle of aperture is referred to as flip angle. The magnitude of the flip angle is dependent on the strength and the duration of the applied electromagnetic pulse. In the case of a so-called 90° pulse, the spins are deflected from the z axis to the transverse plane (flip angle 90°).

After termination of the RF pulse, the magnetization relaxes back to the original state of equilibrium, in which the magnetization in the z direction is built up again with a first time constant $T_1$ (spin lattice or longitudinal relaxation time), and the magnetization in the direction perpendicular to the z direction relaxes with a second time constant $T_2$ (spin-spin or transverse relaxation time). The variation of the magnetization can be detected by means of receiving RF coils which are arranged and oriented within an examination volume of the MR device in such a manner that the variation of the magnetization is measured in the direction perpendicular to the z-axis. The decay of the transverse magnetization is accompanied, after application of, for example, a 90° pulse, by a transition of the nuclear spins (induced by local magnetic field inhomogeneities) from an ordered state with the same phase to a state in which all phase angles are uniformly distributed (dephasing). The dephasing can be compensated by means of a refocusing pulse (for example a 180° pulse). This produces an echo signal (spin echo) in the receiving coils.

To realize spatial resolution in the body, constant magnetic field gradients extending along the three main axes are superposed on the uniform magnetic field, leading to a linear spatial dependency of the spin resonance frequency. The signal picked up in the receiving coils then contains components of different frequencies which can be associated with different locations in the body. The signal data obtained via the receiving coils corresponds to the spatial frequency domain and is called k-space data. The k-space data usually includes multiple lines acquired with different phase encoding. Each line is digitized by collecting a number of samples. A set of k-space data is converted to a MR image by means of an image reconstruction algorithm.

MR imaging of the breast is well established in clinical practice for the diagnosis of cancer. It is known to provide high sensitivity and reasonable specificity in differentiating benign and malignant lesions. Dynamic contrast enhanced MR imaging (DCE) using Gd-DTPA as contrast agent is the most important method for detecting breast lesions and to differentiate between benign and malignant lesions. However, the use of contrast agents in MR imaging has recently more and more become a concern in terms of patient safety.

Electric properties tomography (EPT) is a novel technique using MR imaging to investigate the electric conductivity of tissue (see, e.g., WO 2007/017779 A2). The conductivity can be obtained from a simple and common imaging sequence (e.g. a turbo spin echo sequence) without injection of a contrast agent. The excitation of magnetic resonance is related to the spatial RF (magnetic) field distribution. The RF field distribution can be measured directly using conventional $B_1$ mapping techniques. The unknown electric conductivity can then be calculated from a measured phase map, at least within a homogeneous tissue area, wherein the phase map represents the spatial RF field distribution induced by the RF pulses in the object. To ensure that boundary artifacts are excluded in this calculation, a precise anatomical knowledge of tissue boundaries is required for derivation of an electric conductivity map from the acquired MR signal data.

It has been shown that factors exist that lead to elevated electric conductivity in malignant tumors. Hence, EPT has been studied as a possible candidate for a non-contrast enhanced MR imaging method for the diagnosis of cancer. Several studies have shown that the electric conductivity of a brain tumor is higher than that of surrounding normal white matter and that a relationship between the electric conductivity of normal and cancerous tissue in the breast exists. A comparison of EPT with standard DCE imaging has been performed to investigate the ability to differentiate between benign and malignant breast lesions (Mori N. et al., "Diagnostic value of electric properties tomography (EPT) for differentiating benign from malignant breast lesions: comparison with standard dynamic contrast-enhanced MRI", Eur. Radiol., 2018). In this study, DCE imaging has been used to ensure sensitivity of lesion detection while EPT was used for the characterization of lesions detected by DCE.

Hence, up to now, EPT in most cases relies on the administration of a contrast agent because a precise knowledge of tissue (tumor) boundaries is required. In the study cited above, the tissue boundaries required for the EPT reconstruction are derived from the DCE images. This approach has two disadvantages: (a) although tumor characterization is essentially performed via EPT, a contrast agent is still needed as a priori input for EPT, (b) the MR signal data for EPT and DCE are acquired in two separate scans thus requiring image registration, which is a non-trivial task due to flexibility of tissue and potential scan-specific geometric image distortions. The known method is thus prone to registration errors.

EP 3 378 426 A1 discloses a method for locating ablated tissues using EPT. Therein, a balanced Fast Field Echo (bFFE) sequence is used. A conductivity map is reconstructed from phase information wherein a bilateral median filter is applied using tissue boundary information delineated from a magnitude image reconstructed from the bFFE data.

SUMMARY OF THE INVENTION

From the foregoing it is readily appreciated that there is a need for an improved MR imaging method for the detection, delineation and specification of cancerous lesions that does not require contrast media. It is consequently an object of the invention to enable MR signal acquisition in a single scan providing the necessary information for EPT, namely a phase map as well as tissue boundaries for tumor delineation. In the best case, such an MR image acquisition technique exhibits a tumor detection sensitivity comparable to DCE.

In accordance with the invention, a method of MR imaging of an object placed in an examination volume of a MR device is disclosed. The method comprises the steps of:
subjecting the object to a multi echo steady state imaging sequence comprising RF pulses and switched magnetic field gradients, wherein two or more echo signals are generated in each interval between successive RF pulses, wherein the imaging sequence comprises diffusion weighting magnetic field gradients;
acquiring the echo signals in a number of repetitions of the imaging sequence;
deriving at least one magnitude image and at least one phase map from the acquired echo signals, which phase map represents the spatial RF field distribution induced by the RF pulses in the object; and
reconstructing an electric conductivity map from the MR image and from the phase map, wherein boundaries between normal and suspicious tissues are derived on the basis of diffusion weighting in the at least one magnitude image as a prerequisite for reconstructing the electric conductivity map from the phase map.

The invention proposes, in other words, to use a multi-echo steady state imaging sequence to acquire MR signal data in a single scan. Both the phase map and the tissue contrast (to derive the boundaries between different tissue types) are obtained from the acquired echo signals thus allowing the reconstruction of the desired electric conductivity map. No error-prone registering of the image data of two independent scans, as in the prior art, is necessary and, more importantly, no contrast agent needs to be administered to the object (the patient).

In general, steady state imaging sequences are based on a gradient echo imaging sequence with a short repetition time. Steady state sequences include transverse coherences from overlapping multi-order spin echoes and stimulated echoes. This is usually accomplished by refocusing the phase-encoding gradient in each repetition interval in order to keep the phase integral (or gradient moment) constant. Fully balanced steady state imaging sequences achieve a phase of zero by refocusing all imaging gradients.

Diffusion sensitivity is induced in the steady state imaging sequence by adding diffusion weighting magnetic field gradients. By using a strong diffusion gradient moment in the steady state sequence, the resulting diffusion weighting highlights tumors with positive contrast as areas of restricted diffusion and thus enables to distinguish tumor and ductal tissue (see Granlund K. L. et al., "High-resolution, three-dimensional diffusion-weighted breast imaging using DESS", Magn. Reson. Imaging., 2014, 32, 330-341). DESS ("dual echo steady state") generates two echo signals between successive RF pulses, namely a free induction decay (FID) signal and an echo signal from the steady state free precession of the magnetization individually in each repetition. Phase encoding magnetic field gradients are balanced to maintain the steady state of transverse magnetization. The collection of two signals (FID and echo signals) provides a means to correct for relaxation weighting and further provides the diffusion weighting and, thus, excellent tumor contrast in the magnitude image such that lesions can be detected and boundaries between normal and suspicious tissues can be derived as a prerequisite for phase-based conductivity imaging.

The phase map is suitable for EPT if it only relates to $B_1$, and is not influenced by inhomogeneity of the main magnetic field $B_0$. Conventionally, any unwanted influence of $B_0$ inhomogeneity is avoided by using spin echo based imaging sequences. The invention exploits that unwanted $B_0$ inhomogeneity influences on the phase map are negligible in steady state acquisitions, because the phase remains almost unchanged for off-resonances within the pass band (frequency range corresponding to 1/TR). In a DW-DESS acquisition, e.g., the $B_1$-related phase map can directly be derived for each position in a reconstructed complex MR image from the real and imaginary parts of the respective image value. The same holds in principle for other multi echo steady state imaging sequences, like, e.g., TESS ("Triple-echo steady state", see Kraff O. et al., "7 Tesla quantitative hip MRI: a comparison between TESS and CPMG for $T_2$ mapping", Magnetic Resonance Materials in Physics, Biology and Medicine, 2016, 29(3), 503-512).

In a preferred embodiment, two or more complex MR images are reconstructed such that each of the complex MR images is associated with one echo time value, i.e. one subset of echoes of the multi echo steady state imaging sequence. In the case of a DESS imaging sequence, two MR images are obtained from the two echoes generated in each interval between two successive RF pulses (or three MR images in the case of a TESS imaging sequence). A magnitude image and a phase map can then be derived from each complex MR image. In all cases, the MR images associated with the different echoes yield in principle the same phase map, but, of course, the magnitude images differ in their contrast. This can be utilized for reconstructing the electric conductivity map. Preferably, independent conductivity maps are calculated from the different sets of magnitude images and phase maps, and the conductivity maps are then combined into a final conductivity map, either by simple superposition (to obtain an average conductivity map as the final result) or by weighted averaging taking the signal-to-noise-ratio (SNR) into account such that the conductivity is taken at each image position with the largest SNR at the respective position.

In order to suppress signal contributions from fat in applications like breast cancer diagnosis, the steady state sequence is preferably performed with additional fat suppression, e.g. by employing spectrally selective RF pulses (water only excitation).

Tissue boundary determination can be improved by taking multiple magnitude images into account. For example, an edge detection algorithm, like the known Sobel or Canny algorithm, can be used and the results can be combined by straight-forward superposition or by locally weighted averaging.

In a further preferred embodiment, the step of deriving tissue boundaries involves a segmentation of the magnitude image (or multiple magnitude images). A known segmentation technique may be employed, such as, e.g. deep learning (DL)-based image segmentation, preferably using (regional) convolutional neuronal networks (CNN). Segmentation is the process of partitioning the magnitude image(s) into multiple regions that share similar attributes, thus yielding the boundaries between different tissue types (healthy tissue vs. suspicious/cancerous tissue). Image segmentation has recently become the biggest target for DL approaches in medical imaging. MR image segmentation using DL, typically CNNs, has been proposed in almost the whole field of applications, whereof breast and brain tumor segmentation are only examples.

The method of the invention described thus far can be carried out by means of a MR device including at least one main magnet coil for generating a uniform static magnetic field within an examination volume, a number of gradient coils for generating switched magnetic field gradients in different spatial directions within the examination volume, at least one RF coil for generating RF pulses within the examination volume and/or for receiving MR signals from an object positioned in the examination volume, a control unit for controlling the temporal succession of RF pulses and switched magnetic field gradients, and a reconstruction unit. The method of the invention can be implemented, for example, by a corresponding programming of the reconstruction unit and/or the control unit of the MR device.

The method of the invention can be advantageously carried out in most MR devices in clinical use at present. To this end it is merely necessary to utilize a computer program by which the MR device is controlled such that it performs the above-explained method steps of the invention. The computer program may be present either on a data carrier or be present in a data network so as to be downloaded for installation in the control unit of the MR device.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings.

DETAILED DESCRIPTION OF THE EMBODIMENTS

Figure 1:
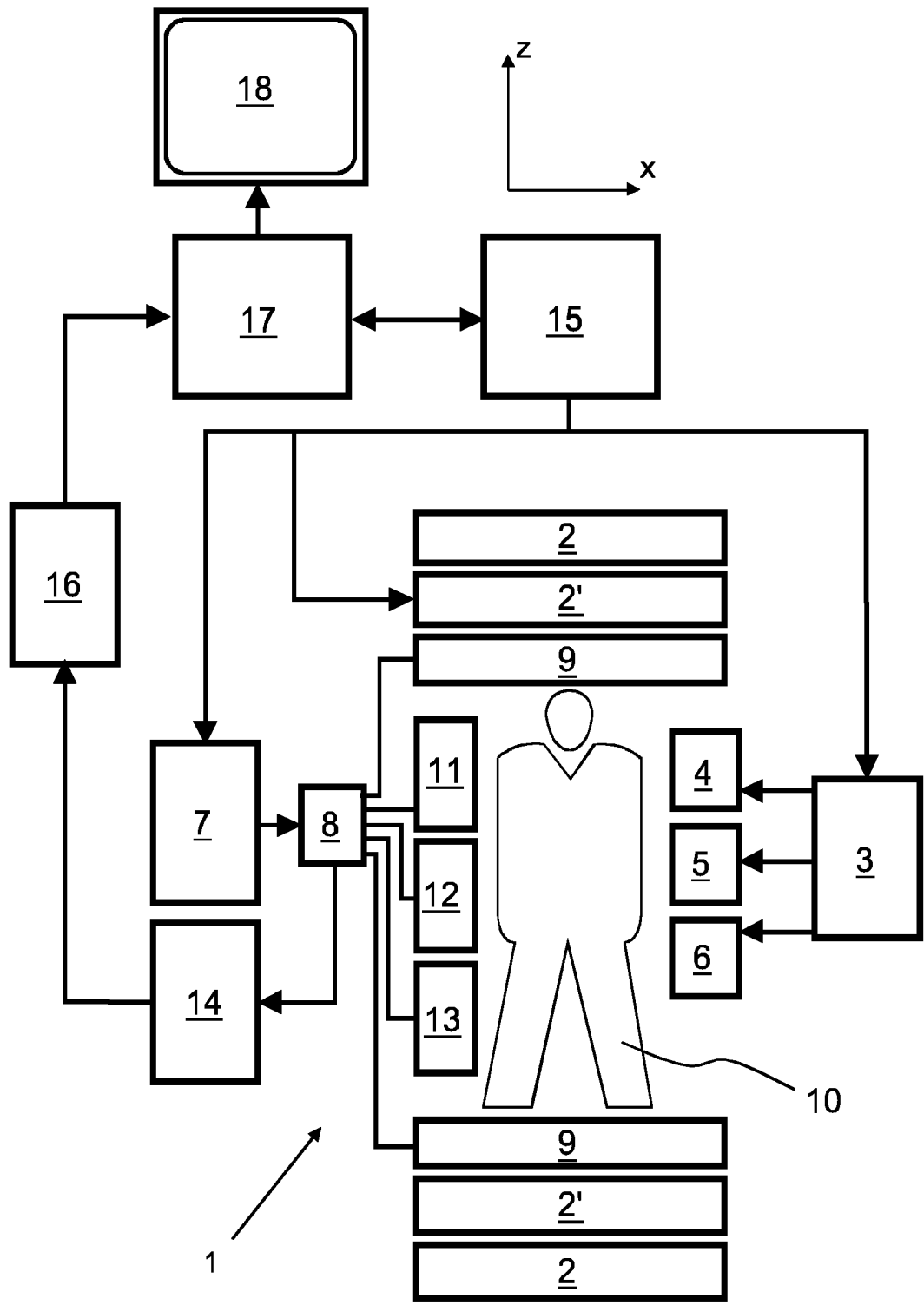
FIG. 1 shows a MR device for carrying out the method of the invention.

With reference to FIG. 1, a MR device 1 is shown. The device comprises superconducting or resistive main magnet coils 2, 2' such that a substantially uniform, temporally constant main magnetic field is created along a z-axis through an examination volume.

A magnetic resonance generation and manipulation system applies a series of RF pulses and switched magnetic field gradients to invert or excite nuclear magnetic spins, induce magnetic resonance, refocus magnetic resonance, manipulate magnetic resonance, spatially and otherwise encode the magnetic resonance, saturate spins, and the like to perform MR imaging.

More specifically, a gradient pulse amplifier 3 applies current pulses to selected ones of whole-body gradient coils 4, 5 and 6 along x, y and z-axes of the examination volume. A digital RF transmitter 7 transmits RF pulses or pulse packets, via a send-/receive switch 8, to a whole-body volume RF coil 9 to transmit RF pulses into the examination volume. A typical MR imaging sequence is composed of a packet of RF pulse segments of short duration which taken together with each other and any applied magnetic field gradients achieve a selected manipulation of nuclear magnetic resonance. The RF pulses are used to saturate, excite resonance, invert magnetization, refocus resonance, or manipulate resonance and select a portion of a body 10 positioned in the examination volume. The 1\4R signals are also picked up by the whole-body volume RF coil 9.

For generation of MR images of limited regions of the body 10, a set of local array RF coils 11, 12, 13 are placed contiguous to the region selected for imaging. The array coils 11, 12, 13 can be used to receive MR signals induced by body-coil RF transmissions.

The resultant MR signals are picked up by the whole body volume RF coil 9 and/or by the array RF coils 11, 12, 13 and demodulated by a receiver 14 preferably including a preamplifier (not shown). The receiver 14 is connected to the RF coils 9, 11, 12 and 13 via send-/receive switch 8.

A host computer 15 controls the gradient pulse amplifier 3 and the transmitter 7 to generate any of a plurality of MR imaging sequences, such as a diffusion weighted dual echo steady state (DW-DESS) imaging sequence or the like. For the selected sequence, the receiver 14 receives a single or a plurality of MR data lines in rapid succession following each RF excitation pulse. A data acquisition system 16 performs analog-to-digital conversion of the received signals and converts each MR data line to a digital format suitable for further processing. In modern MR devices the data acquisition system 16 is a separate computer which is specialized in acquisition of raw image data.

Ultimately, the digital raw image data is reconstructed into an image representation by a reconstruction processor 17 which applies a Fourier transform or other appropriate reconstruction algorithms, such as SENSE, SMASH, or GRAPPA. The MR image may represent a planar slice through the patient, an array of parallel planar slices, a three-dimensional volume, or the like. The image is then stored in an image memory where it may be accessed for converting slices, projections, or other portions of the image representation into appropriate format for visualization, for example via a video monitor 18 which provides a man-readable display of the resultant MR image.

With continuing reference to FIG. 1 and with further reference to FIG. 2 an embodiment of the method of the invention is explained in the following.

The body 10 is subjected to a diffusion weighted steady state imaging sequence. The generated echo signals are acquired and reconstructed into a complex diffusion weighted MR image of the brain. A magnitude image is derived from the complex MR image. FIG. 2a shows the resulting DESS magnitude image. Furthermore, the $B_1$-related phase map indicating the spatial $B_1$ distribution in the object 10 is directly derived for each position in the reconstructed MR image from the real and imaginary parts of the respective image value S:

φ(r)=atan 2(Im(S),Re(S))

FIG. 2b shows the resulting phase map. The diffusion contrast of the magnitude image shown in FIG. 2a is used to derive boundaries between grey and white matter in the brain image. Finally, the phase information and the tissue boundaries are used to compute an electric conductivity map according to the conventional phase-based EPT method. The resulting electric conductivity map is shown in FIG. 2c.

Figure 2:
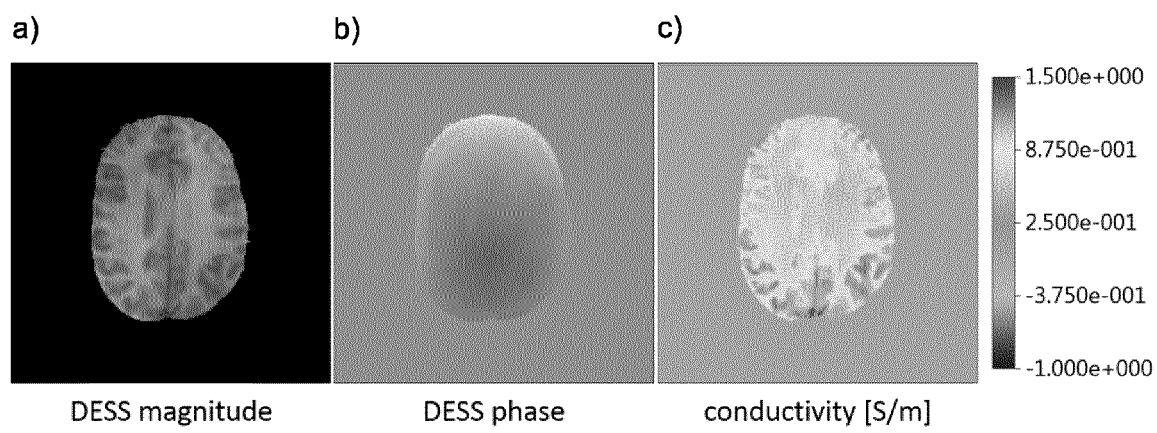
FIG. 2 shows example MR images illustrating the approach of the invention.

Although FIG. 2 shows an example of brain imaging to demonstrate the general feasibility of the method of the invention, the main potential of the invention is seen in MR-based, contrast agent-free diagnosis (screening) of breast cancer.

The invention claimed is:

1. A method of magnetic resonance (MR) imaging of an object placed in an examination volume of a MR device, the method comprising:
    subjecting the object a multi echo steady state imaging sequence comprising RF pulses and switched magnetic field gradients, wherein two or more echo signals are generated in each interval between successive RF pulses, wherein the imaging sequence comprises diffusion weighting magnetic field gradients;
    acquiring the echo signals in a number of repetitions of the imaging sequence;
    deriving at least one magnitude image and at least one phase map from the echo signals, which phase map represents the spatial RF field distribution induced by the RF pulses in the object; and
    reconstructing an electric conductivity map from the magnitude image and from the phase map, wherein boundaries between normal and suspicious tissues are derived on the basis of diffusion weighting in the at least one magnitude image as a prerequisite for reconstructing the electric conductivity map from the phase map.

2. The method of claim 1, wherein two or more complex MR images are reconstructed such that a magnitude image and a phase map derived from each complex MR image is associated with each of the echoes generated in each interval between two successive RF pulses.

3. The method of claim 2, wherein an individual electric conductivity map is reconstructed from each magnitude image and phase map.

4. The method of claim 3, wherein the individual electric conductivity maps are combined into a single final electric conductivity map.

5. The method of claim 1, wherein the imaging sequence employs fat suppression.

6. The method of claim 1, wherein the step of deriving tissue boundaries involves a segmentation of the one or more magnitude images.

7. The method of claim 1, wherein an edge detection algorithm is used for deriving the tissue boundaries.

8. A computer program stored on a non-transitory computer readable medium to be run on a magnetic resonance (MR) device, which computer program comprises instructions for carrying out the method of claim 1.

9. A magnetic resonance (MR) device including at least one main magnet coil for generating a uniform, static magnetic field within an examination volume, a number of gradient coils for generating switched magnetic field gradients in different spatial directions within the examination volume, at least one RF coil for generating RF pulses within the examination volume and/or for receiving MR signals from an object positioned in the examination volume, a control unit for controlling the temporal succession of RF pulses and switched magnetic field gradients, and a reconstruction unit, wherein the MR device configured to perform a method comprising:
    subjecting the object to a multi echo steady state imaging sequence comprising RF pulses and switched magnetic field gradients, wherein two or more echo signals are generated in each interval between successive RF pulses, wherein the imaging sequence comprises diffusion weighting magnetic field gradients;
    acquiring the echo signals in a number of repetitions of the imaging sequence;
    deriving at least one magnitude image and at least one phase map from the acquired echo signals, which phase map represents the spatial RF field distribution induced by the RF pulses in the object; and
    reconstructing an electric conductivity map from the magnitude image and from the phase map, wherein boundaries between normal and suspicious tissues are derived on the basis of diffusion weighting in the at least one magnitude image as a prerequisite for reconstructing the electric conductivity map from the phase map.

* * * * *